United States Patent [19]

Regen

[11] Patent Number: 4,943,624
[45] Date of Patent: Jul. 24, 1990

[54] SUPRAMOLECULAR SURFACTANTS: AMPHIPHILIC POLYMERS DESIGNED TO DISRUPT LIPID MEMBRANES

[75] Inventor: Steven L. Regen, Bethlehem, Pa.

[73] Assignee: Lehigh University, Bethlehem, Pa.

[21] Appl. No.: 263,871

[22] Filed: Oct. 28, 1988

[51] Int. Cl.⁵ .............. C07C 69/34; C08G 63/66; A61K 31/745; A61K 7/00
[52] U.S. Cl. .................. 528/301; 560/198; 424/78; 514/844
[58] Field of Search .......... 528/301; 560/198; 424/78; 514/844

[56] References Cited

U.S. PATENT DOCUMENTS 2,562,878  1/1949  Blair ........................ 560/198
3,067,178  12/1962  Greenberg et al. ............ 560/198
4,549,009  10/1985  Higaki et al. ................ 528/301

FOREIGN PATENT DOCUMENTS 659631  3/1963  Canada ......................... 560/198

Primary Examiner—Joseph L. Schofer
Assistant Examiner—Carmen B. Pili-Curtis
Attorney, Agent, or Firm—Oblon, Spivak, McClelland, Maier & Neustadt

[57] ABSTRACT

An amphiphilic polymer, having the monomer unit structure A, B, C or D:

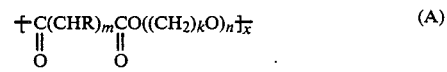

wherein R is at least one H and $C_{1-6}$ alkyl, $k=1-4$, $m=4-30$, $n=2-50$ and $x=2-500$.

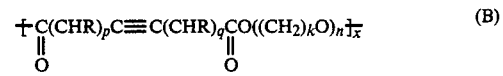

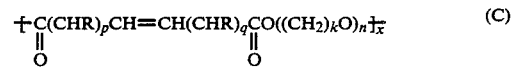

wherein p and q are, independently, 0–22, and the sum of p and q is 4–22;

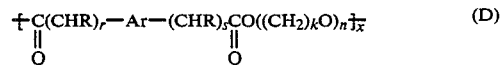

wherein r and s are, independently, 0–22, and the sum of r and s is in the range 2–44, Ar is a divalent aromatic radical; and compounds in which the ester group in compounds A, B, C and D is replaced by an amide, urea, urethane, ether or carbonate. These compounds are useful for disrupting lipid membranes, as surfactants and dispersing agents and in the treatment of viral, bacterial and fungal diseases.

7 Claims, 8 Drawing Sheets

SUPRAMOLECULAR SURFACTANTS: AMPHIPHILIC POLYMERS DESIGNED TO DISRUPT LIPID MEMBRANES

BACKGROUND OF THE INVENTION

1. Field of the Invention:

The invention relates to amphiphilic polymers which may be used to disrupt lipid membranes, pharmaceutical compositions containing these polymers and their use in the treatment of viral, fungal and bacterial infections. More specifically, the amphiphilic polymers are prepared from polyalkylene glycols and dicarboxylic acids or derivatives thereof.

2. Discussion of the Background:

Biological organisms such as viruses, bacteria and fungi commonly utilize lipid membranes in their biological structure. These lipid membranes are generally lipid monolayers or bilayers composed of amphipathic membrane lipids. The amphipathic membrane lipids contain both a hydrophilic and a hydrophobic segment and are arranged in space so that the polar hydrophilic segments of the amphipathic lipids are oriented toward the outside of the membrane. Lipid bilayers may occur in various forms, including planar bilayer membranes as well as lipid vesicles.

Disruption of the lipid membrane of a biological organism can cause severe structural and metabolic damage to the organism due to loss of structural integrity, electrolyte loss, etc. The inactivation of the human immunodeficiency virus (HIV), New Castle disease virus, herpes simplex virus, cytomegalovirus and Semliki forest virus, for example, by perturbing the viral lipid envelope has been proposed (Reimund, E. Lancet, II, 1986, 1159; Aloia, R. C., Jensen, F. C., Curtain, C. C., Mobley, P. W., Gordon, L. M., *Proc. Natl. Acad. Sci.* (USA), 1988, 85, 900).

Compounds which are known to disrupt or solubilize biological membranes include, for example, alkyl and aromatic poly(ethylene glycol)s. These compounds are alkyl and aryl ethers of various poly(ethylene glycol)s and include, for example, Triton® X-100 add reduced derivatives thereof. However, such compounds show little selectivity in disrupting membranes of microorganisms relative to cell membranes.

A need continues to exist for new pharmaceutical compounds useful in the treatment of viral, fungal and bacterial infections. Amphiphilic "supramolecular surfactants" provide a new class of compounds for treatment of these infections.

SUMMARY OF THE INVENTION

Accordingly, one object of the present invention is to provide a new class of compounds which may be used in pharmaceutical compositions for the treatment of viral, fungal and bacterial infections.

Another object of the invention is to provide amphiphilic polymers which may be used in pharmaceutical compositions to disrupt lipid membranes, particularly biological membranes in viral, bacterial and fungal organisms.

These and other objects, which will become apparent from the following specification, have been achieved by the present amphiphilic polymers. The amphiphilic polymers of the present invention include saturated, unsaturated and aromatic polyesters, polyamides, polyureas, polyurethanes, polyethers and polycarbonates derived from poly(alkylene glycol)s and organic diacids or derivatives thereof. The amphiphilic polymers may be incorporated in pharmaceutical compositions and used to disrupt lipid membranes, in the treatment of viral, bacterial and fungal infections and ma also be used as surfactants and/or dispersing agents in health care products such as cosmetics.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing, wherein.

DETAILED DESCRIPTION OF THE PREFERRED EMBODIMENTS

Figure 1:
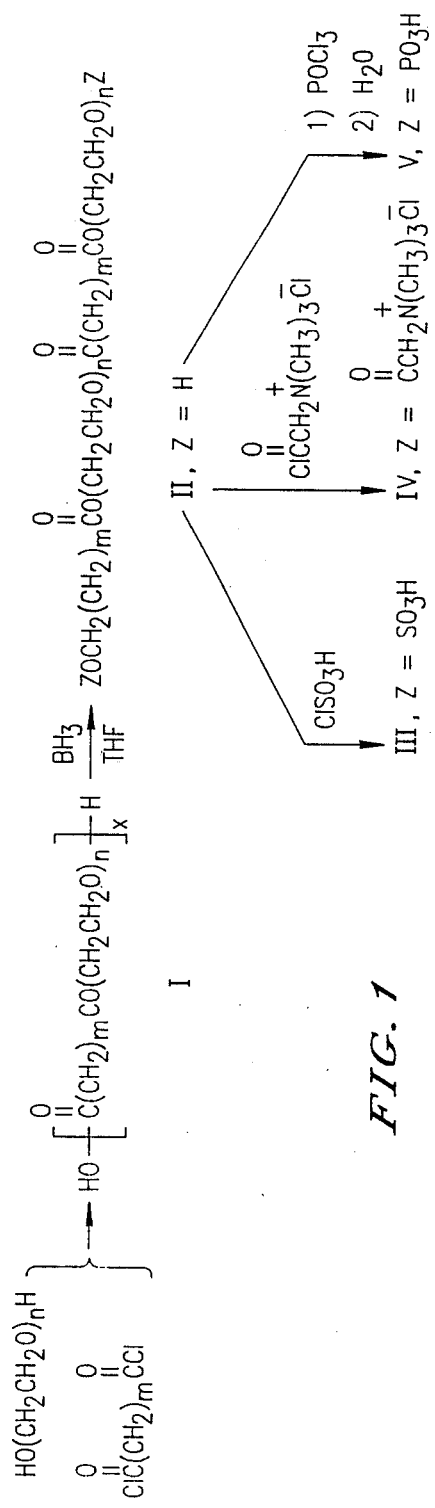
FIGS. 1–6 illustrate synthetic schemes which may be used to prepare the supramolecular surfactants of the present invention.

The present invention is related to the discovery that certain "supramolecular surfactants" exhibit a broad range of activity for disrupting lipid bilayers. While not being limited thereby, the present supramolecular surfactants are thought to act by inserting a series of short hydrocarbon loops into the outer monolayer leaflet of a bilayer membrane, thereby disrupting the membrane. Disruption is thought to be due to (i) a mismatch between the length of the phospholipid chains of the bilayer and the effective length of the penetrating loops, (ii) the difficulty for such loops to align with the lamellar phase of the membrane, and (iii) the perturbation of head group hydration and conformation. Amphiphilic polymers having hydrophobic and hydrophilic segments throughout the backbone, not only bind strongly to lipid bilayers through the multiple sites of attachment, but also maintain a high local concentration of repeating units, that is repeating defects, within the membrane. This high local concentration exists due to the inability of the repeat units, located within the bilayer membrane, to diffuse apart and become diluted.

The surfactant molecules function by "disrupting" lipid membranes. By "disrupting" is meant the rupture of a lipid membrane such that the structural integrity of the membrane is at least partially altered. The alteration of the lipid bilayer may occur over a continuum from slight alterations in the lipid assembly all the way to complete rupture of the membrane. The term "disrupting" includes both leakage of cellular, liposomal, viral, bacterial, and fungal contents through the membrane as well as complete rupture of the membrane structure. Short-lived defects as well as long term structural defects are also considered to be within the scope of the membrane disruption properties of the present compounds.

The supramolecular surfactants of the present invention are polyesters, polyamides, polyureas, polyurethanes, polyethers and polycarbonates prepared from saturated aliphatic, unsaturated aliphatic and aromatic dicarboxylic acids or reactive derivatives thereof with alkylene glycols or polyalkylene glycols. The supramolecular surfactant polymers may be random polymers or may be block copolymers prepared by both solution and solid phase syntheses. The compounds of the present invention will be discussed in more detail below.

The supramolecular surfactants of the present invention may have the repeat unit structure shown below:

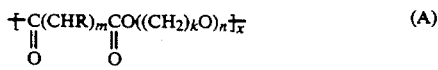
(A)

wherein R is at least one of H and $C_{1-6}$ alkyl, k=1-4, m=4-30, n=2-50, and x=2-500. These amphipathic polymers are prepared by reacting a glycol or polyalkylene glycol with a dicarboxylic acid or a reactive acid derivative thereof.

Polyalkylene glycols suitable for use in preparing these amphipathic polymers include polyalkylene glycols having an average of 2-50 repeating units. Preferred polyalkylene glycols have an average of 4-23 repeating units, with an average in the range of 12-16 being particularly preferred. Suitable polyalkylene glycols are prepared from glycols having 2-5 carbon atoms, for example ethylene glycol, propylene glycols, butylene glycols, etc., and lower alkyl substituted glycols having up to 10 carbon atoms. Particularly preferred are amphipathic polymers prepared from polyethylene glycol.

The dicarboxylic acid used to prepare polymers having structure A is an unsubstituted aliphatic dicarboxylic acid having 4-30, preferably 10-20 carbon atoms or a reactive derivative such as the acid halide, acid anhydride, or diisocyanate thereof. Particularly preferred derivatives are the acid chlorides and diisocyanates. Alternatively, the dicarboxylic acid may be substituted by one or more alkyl groups having from 1-6 carbon atoms. Preferred dicarboxylic acids and diisocyanates are those in which m=10-20, with dicarboxylic acid in which m=12-18 being especially preferred.

The supramolecular surfactants may contain from 2-500 repeating units (x) per surfactant molecule. Preferably, the surfactant polymers contain from 3-50 repeating units with compounds containing 3-20 average repeating units per molecule being especially preferred.

Any of the supramolecular surfactants of formulas A-D, or the amide, urea, urethane, ether or carbonate analogs thereof shown below, may be either non-ionic or ionic depending upon the particular end groups present on the polymer chain. For example, when the end groups are carboxylic acid and hydroxyl groups, the supramolecular surfactant will be substantially non-ionic in character. Supramolecular surfactant molecules which have charged end groups, i.e., cationic, anionic, or zwitterionic end groups (H. Eibel, Liposomes: From Physical Structures to Therapeutic Application, Chapter 3, Ed.—C. G. Knight, Elsevier/North Holland Press, N.Y., 1981, page 35), not only have improved water solubility but also different membrane selectivity than non-ionic surfactant molecules. Preferred ionic end groups include sulfonic acid, trialkylammonium, phosphate, $-OPO_3R'^-$, $-OC(O)CH_2PR'_3{}^+$, $-OC(O)CH_2SR'_2{}^+$, and $-OPO_3CH_2CH_2N(CH_3)_3{}^+$ end groups where the alkyl group (R') is an alkyl, preferably a $C_{1-10}$ alkyl group.

The amphiphilic polymers of the present invention are prepared by condensing the appropriate polyalkylene glycol with the appropriate dicarboxylic acid or dicarboxylic acid derivative using known condensation reactions. For example, solution polymerization reactions may be carried in an appropriate solvent at ambient temperatures and the polymers purified by standard solubilization-precipitation procedures. Preferred solvents include halogenated hydrocarbons such as methylene chloride and chloroform, cyclic and acyclic ethers such as dioxane and tetrahydrofuran, and aromatic hydrocarbons such as toluene and benzene. Solution polymerization using a $CH_2Cl_2$-pyridine (9/1, v/v) at ambient temperature with purification by solubilization-precipitation using $CH_2Cl_2$/hexane has proven to be effective, for example. A synthetic scheme for synthesizing compounds having structure A is shown in FIG. 1.

The supramolecular surfactants of the present invention may also have structures B and C shown below.

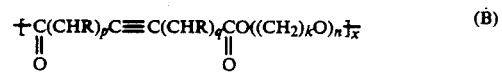
(B)

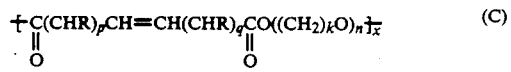
(C)

In structures B and C, R is at least one of H and $C_{1-6}$ alkyl, p and q are, independently, 0-22, where the sum of p and q is in the range 4-44, and n, k and x are as defined above. As in structure A, the glycol monomer units may be substituted with a lower alkyl group. P and q are preferably, and independently, 2-9. The carbon-carbon double bond present in structure C may be in the cis or trans conformation or a mixture of cis and trans may be present.

Figure 2:
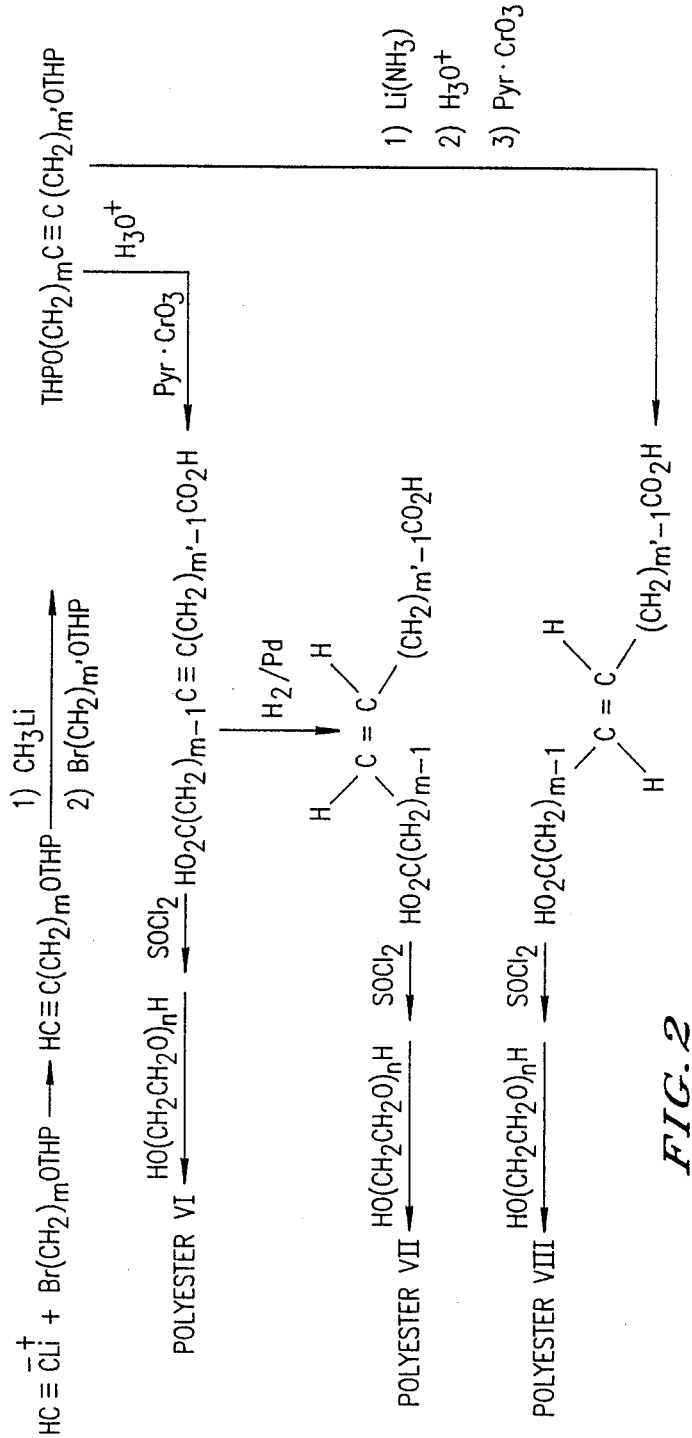

The presence of unsaturated sites in the hydrophobic segment of the supramolecular surfactant molecule significantly effects the polymer interaction with lipid membranes, due primarily to conformational restrictions imposed within the hydrophobic segment by the unsaturation. A synthetic scheme for the preparation of compounds having structures B and C is shown in FIG. 2. The cis/trans carbon-carbon double bonds are prepared by appropriate reduction of an acetylenic precursor to the cis or trans double bond by known synthetic methods. Polymerization of the unsaturated dicarboxylic acid chlorides and the selected alkylene glycol results in unsaturated polyester compounds.

Figure 3:
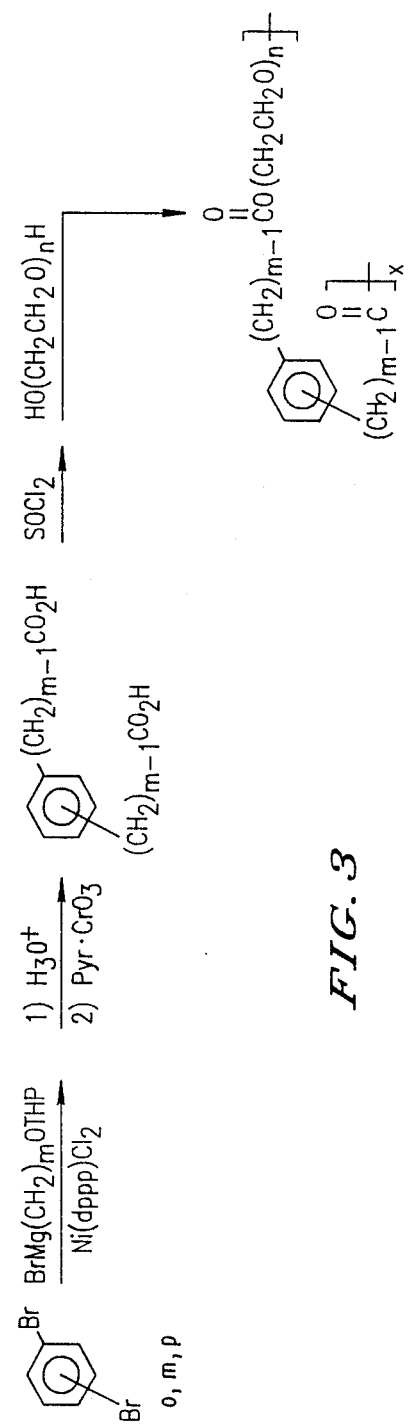

In a further embodiment of the present, the supramolecular surfactant compounds may have structure D shown below:

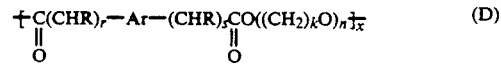
(D)

wherein r and s are, independently, 0-22 and the sum of r and s is in the range 2-44, Ar is a divalent aromatic radical and R, k, n and x are as defined above. The values r and s are preferably, independently, equal to 3-6. Preferably, Ar is an ortho, meta or paraphenylene or naphthylene radical. Additionally, the aromatic radical Ar may contain a hetero atom, such as, for example pyridine, thiophene and furan. A synthetic scheme for the production of an aromatic polyester in which Ar is phenylene is illustrated in FIG. 3.

In addition to polyester surfactant molecules, the present invention includes the corresponding amide, urea, urethane, ether and carbonate analogs of the polyester compounds. In the amide analogs, the ester linkage is replaced with an amide linkage

In the urea and urethane analogs, the ester linkage

is replaced with urea

and urethane

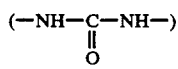

linkages, respectively. In the ether and polycarbonate analogs, the ester is replaced with ether (—O—) and carbonate

Figure 6:
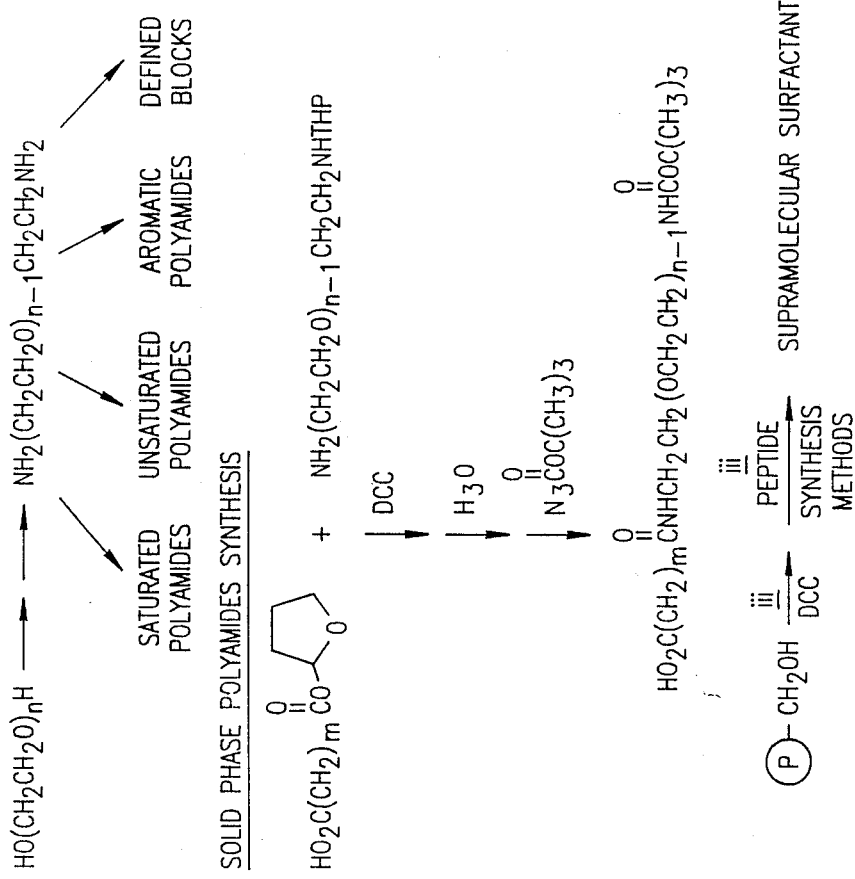

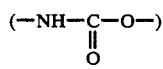

linkages, respectively. A synthetic scheme for the preparation of amide derivatives is illustrated in FIG. 6. In FIG. 6, the encircled "P" represents a polymer particle used in the solid phase polyamide synthesis.

The polyurea and polyurethane analogs may be prepared from the appropriate organic diisocyanates. Organic diisocyanates can be prepared by conventional means, such as for example preparing the diacyl azide and then rearranging the diacyl azide to form the diisocyanate. See for example Advanced Organic Chemistry: Reactions, Mechanisms and Structure, Third Edition, J. March, John Wiley and Sons, 1985, page 984. The diisocyanate can then be used to prepare both the polyurea and polyurethane analogs.

Reaction of the diisocyanate with a polyalkylene glycol produces the polyurethane analog in which the ester linkage in any of structures A–D is replaced with the urethane linkage. Reaction of the diisocyanate with the diamine derivative of a polyalkylene glycol, such as for example $NH_2CH_2CH_2(OCH_2CH_2)_nOCH_2CH_2NH_2$, gives rise to polyurea supramolecular surfactants. In the polyurea structures, the ester linkage in any of structures A–D is replaced with the urea linkage. Examples of both the polyurethane (E) and polyurea (F) structures are shown below (Polymer Chemistry, Malcolm P. Stevens, Addison-Wesley Publ. Co., 1975, page 277).

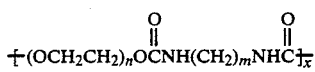 (E)

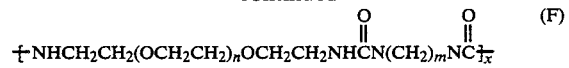 (F)

The polyether analogs can be prepared by either reacting the polyalkylene glycol with an appropriate ditosylate or from the polyalkylene glycol ditosylate with an appropriate diol in the presence of a strong base, such as for example potassium tert-butoxide. The diol can be prepared from the corresponding diacid, i.e., the same diacid used to prepare structures A–D, using known methods. Likewise, the ditosylate can be prepared from this diol using well known methods.

The polycarbonate supramolecular surfactant analogs can be prepared by reacting an appropriate diol with phosgene to form the dichlorocarbonate which may then be reacted with a polyalkylene glycol to prepare the final polycarbonate analog. Examples of the polyether (G) and polycarbonate (H) analogs are shown below. Structures E–H are examples in which the polyalkylene glycol is polyethylene glycol. However, it is to be understood that the alkylene glycol may comprise other glycols such as those noted above.

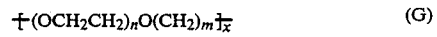 (G)

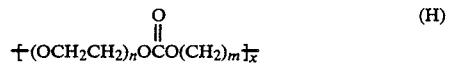 (H)

The ether linkage in the polyether analogs is very stable, particularly under biological conditions. Accordingly, in applications where long lifetimes of the supramolecular surfactants are desired, the polyether analog will provide stability in biological environments. In contrast, the polycarbonate, polyester and polyamide analogs contain biodegradable linkages, i.e., linkages which may be degraded in biological systems. These biodegradable analogs are useful in applications in which biodegradability is a desirable property. Particular applications are in the cosmetic and health care fields, such as for example, as replacements for conventional nonionic surfactants, such as polyalkylene glycols and glycol ethers, which are used as surfactants and dispersing agents in shampoos, soaps, lotions, toothpastes, and creams. Examples of typical applications in which the present supramolecular surfactants are used to substitute for conventional surfactants and surface active agents are disclosed in U.S. Pat. Nos. 4,533,545; 4,708,813; 4,450,091; 4,443,353 and 3,956,401, incorporated herein by reference. Such cosmetic and health care products may be formulated with conventional cosmetic bases.

The polyester, polyamide, polyurea, polyurethane, polyether and polycarbonate supramolecular surfactants of the present invention include random or statistical polymers. The random or statistical polymers are prepared by conventional solution polymerization reactions which result in condensation of the carboxylic acid or acid derivative with the alkylene glycol and give rise to mixtures of product polymers having a distribution of the total number of monomer units in the polymer chain. Fractionation methods may be used to obtain relatively narrow high and low molecular weight polymer samples. Accordingly, the number of monomer units in the supramolecular surfactant polymers need not be expressed as an integer value, but may be expressed as a fractional value.

Figure 4:
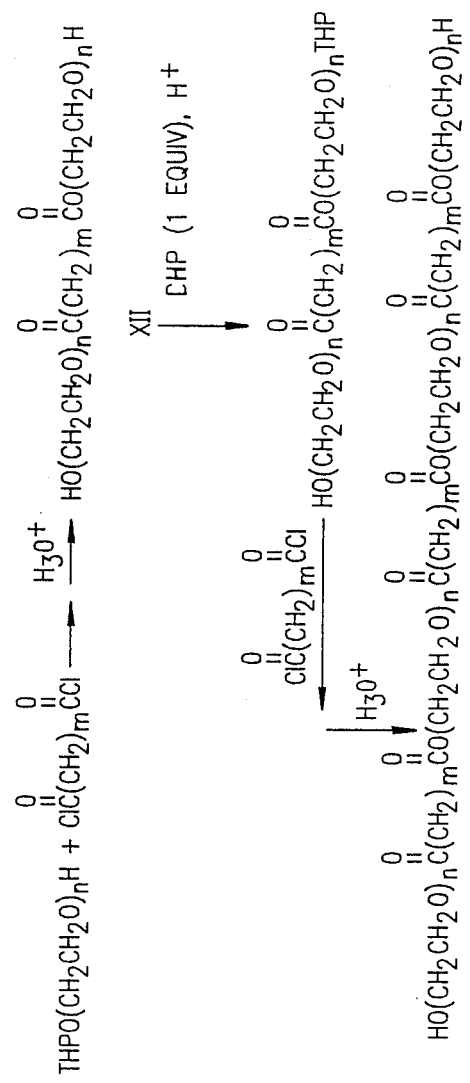
Figure 5:
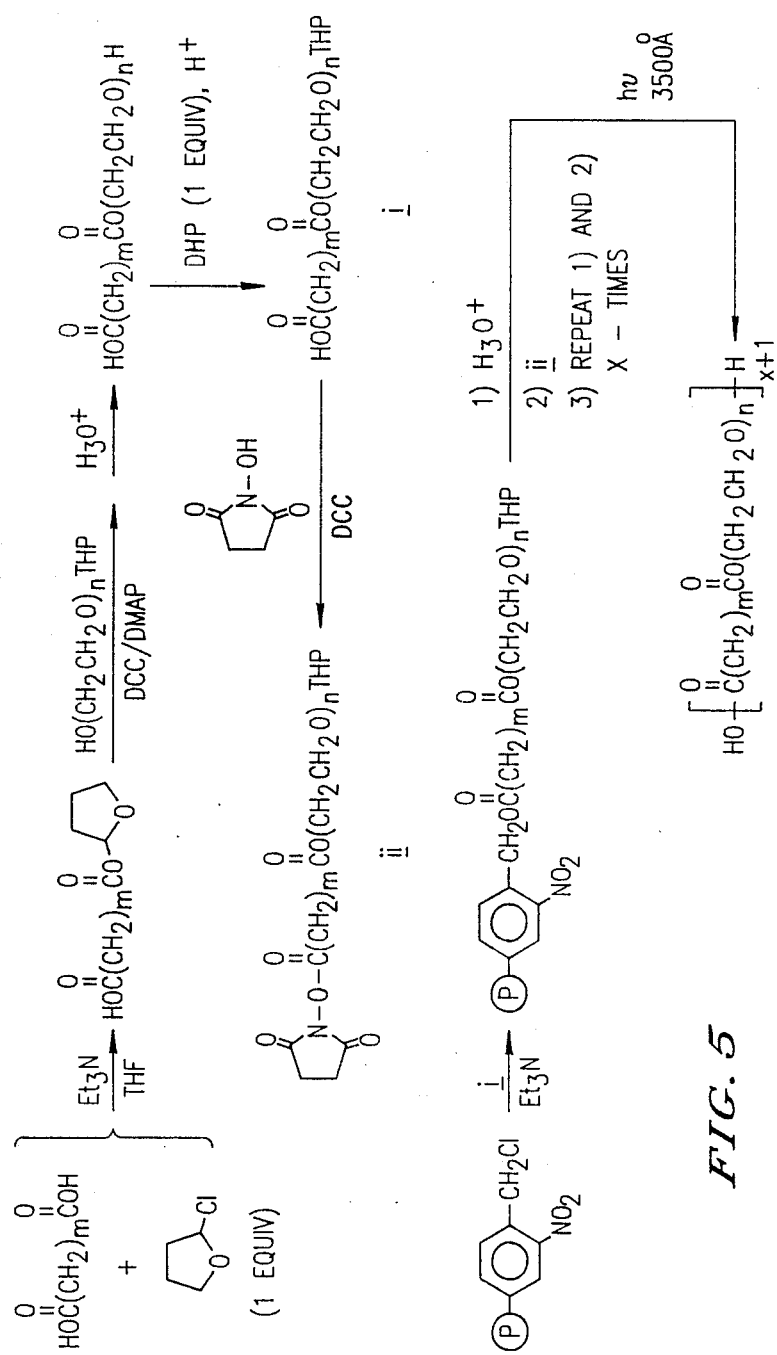

If surfactant molecules having a more clearly defined number of repeat units are desired, it is possible to synthesize polymers having a single number of repeat units using sequential solution and solid phase methods. Additionally, it is possible to prepare supramolecular surfactant molecules having a specific sequence of hydrophobic and hydrophilic segments through the use of solid phase synthetic methods. For example, it is possible to prepare polyesters containing an alternating sequence of hydrophobic units having high hydrophobicity (large numbers of methylene groups) and low hydrophobicity (a lesser number of methylene groups), respectively. Synthetic schemes for solution and solid phase syntheses of the present compounds are shown in FIGS. 4 and 5.

It is to be understood that reagents, reactions and conditions not shown in FIGS. 1–6 may be substituted for those shown as necessary or desirable. Alternative reagents, reactions and conditions will be readily apparent to those skilled in the art.

The ability to prepare several supramolecular surfactant analogs (A–H), as well as the flexibility in preparing statistical, block and sequenced block copolymers gives one great flexibility in designing a supramolecular surfactant for a particular end use. For example, the hydrophobic/hydrophilic properties of the polymer may be designed so as to provide a specific membrane interaction, thereby causing membrane disruption in a particular biological organism or membrane structure. Clearly, the compounds of the present invention may be used both for in vitro and in vivo applications.

Additionally, the degree of polymerization of the alkylene oxide repeating units and the specific alkylene oxide used may be modified to control the membrane disrupting potential of the supramolecular surfactant. By varying these respective properties, it is possible to alter the activity of the present compounds over a very wide range, and thereby tailor the membrane disrupting properties to a single type of organism or class of organisms. In this manner, effective pharmaceutical agents are provided for the treatment of specific viral, bacterial and fungal infections.

The amphiphilic polymers of the present invention may be formulated into pharmaceutical agents for the treatment of viral, fungal and bacterial infections. Of particular interest is the use of the present compounds for the treatment of infection by retroviruses such as HIV (HTLV-III/LAV) which causes acquired immunodeficiency syndrome (AIDS). The invention is therefore also directed to a method of treating AIDS by administering to a mammal infected with a HIV retrovirus one or more compounds of the present invention. Other viruses such as herpes virus, may also be treatable with the compounds of the present invention.

Humans and animals suffering from diseases caused by, for example, HIV virus or bacterial or fungal infections can be treated by administering to the animal patient a pharmaceutically effective amount of one or more of the present compounds, optionally, but preferably in the presence of a pharmaceutically acceptable carrier or diluent.

There may also be included pharmaceutically compatible binding agents, and/or adjuvant materials. The active materials can also be mixed with other active materials which do not impair the desired action and/or which supplement the desired action. The active materials according to the present invention can be administered by any route, for example, orally, parentally, intravenously, intradermally, subcutaneously, or topically, in liquid or solid form. For injection purposes, the medium used will be a sterile liquid. As an injection medium, it is preferred to use water which contains the stabilizing agents, solubilizing agents and/or buffers conventional in the case of injection solutions. Desirable additives include, for example, tartrate and borate buffers, ethanol, dimethylsulfoxide, complex forming agents (for example, ethylene diamine tetraacetic acid), high molecular weight polymers (for example, liquid polyethylene oxide) for viscosity regulation or polyethylene derivatives of sorbitan anhydrides.

Solid carrier materials include, for example, starch, lactose, mannitol, methyl cellulose, talc, highly dispersed silicic acid, high molecular weight fatty acids (such as stearic acid), gelatin, agar, calcium phosphate, magnesium stearate, animal and vegetable fats or solid high molecular weight polymers (such as polyethylene glycols). Compositions suitable for oral administration can, if desired, contain flavoring and/or sweetening agents.

A preferred mode of administration of the compounds of this invention is oral. Accordingly, the compounds may be formulated preferably into solid or liquid form.

The active materials according to the present invention can be employed in dosages and amounts which are determined by conventional methods in the art of pharmacology. Thus, the materials can be used at a dosage range in humans of from 0.1 to 150.0 g/75 kg total body weight/day. A more preferred range lies between 1.0 to 25.0 g/75 kg total body weight/day. The dosages may be administered at once, or may be divided into a number of smaller doses to be administered at varying intervals of time.

The compounds of the present invention are expected to be useful in treating mammals, including humans. Other mammals include dogs, cats, monkeys, horses, and the like.

The ability of the present supramolecular surfactants to disrupt lipid membranes may be analyzed by their ability to induce the release of liposome-encapsulated 5(6)-carboxyfluorescein (Weinstein, J. N., Ralston, E., Leserman, L. D., Klausner, R. D., Dragsten, P., Henkart, P. Blumenthal, R., *Liposome Technology*, G. Gregoriadis (Ed), Vol III, p 183 (1984), CRC Press, Inc., Boca Raton, Fla.)

For example, unilamellar vesicles (about 1000 Å diameter) may be prepared from egg-yolk phosphatidylcholine by standard extrusion procedures using 0.1 μm Nuclepore membranes (Hope, M. J., Bally, M. B., Webb, G., Cullis, P. R., *Biochim. Biophys. Acta*, 1985, 812, 55.), using an aqueous solution of the carboxyfluorescein. The result is a dispersion of lipid vesicles. Aliquots of the lipid dispersion are then incubated with varying concentrations of the supramolecular surfactants and assayed for the release of carboxyfluorescein according to known methods (Weinstein et al, supra). Dynamic light scattering, transmission electron microscopy and gel filtration methods may be used to establish size and size distribution of the vesicles, before and after interaction with supramolecular surfactants. The release of carboxyfluorescein is monitored by fluorescence methods. The percentage of the released carboxyfluorescein (I) is then calculated according to the equation $$I(\%) = \frac{100(I_a - I_b)}{(I_x - I_b)}$$

wherein $I_x$ is the 100% fluorescence intensity determined using an excess of Triton X-100, and $I_b$ and $I_a$ are the fluorescence intensities before and after incubation with surfactant, respectively.

The biological activity of the present compound can be accessed using known methods. For example, the in vitro anti-HIV-1 activity of the polymers can be analyzed in lymphocytes using established human T-lymphocyte cell lines, such as H9, bearing the CD4 receptor (Sarin, P. S.; Sun, D.; Thornton, A.; Muller, W. E., Journal of the National Cancer Institute, 1987, 78, 663; Popovic, M. et al. *Science*, 1984, 224, 497; Reed, L. J., Muench, H., *Am. J. Hyg.*, 1938, 27, 493). Anti-HIV-1 activity in primary human monocytemacrophages and the inhibition of HIV-1 induced syncytium formation by the present compounds may also be used to evaluate the anti-viral activity of the present compounds.

Other features of the invention will become apparent during the course of the following descriptions of exemplary embodiments which are given for illustration of the invention and are not intended to be limiting thereof.

EXAMPLES

Polymers 1-6 shown below were prepared by condensation of the appropriate poly(ethylene glycol)s and acid dichlorides by solution polymerization in $CH_2Cl_2$/pyridine (9/1, v/v) at ambient temperature. The polymers were purified by repeated solubilization-precipitation using $CH_2Cl_2$/hexane. The average number of repeat units per polymer chain ($x_{av}$) was determined by known end group analysis. Large unilamellar vesicles (ca. 1000 Å diameter) were prepared from eggyolk phosphatidylcholine via standard extrusion procedures (0.1 μ Nuclepore membranes), using an aqueous solution of 5(6)-carboxyfluorescein (250 mM, pH 7.4); non-entrapped carboxyfluorescein was moved by gel filtration using a Sephadex G-50 column and a 10 mM borate buffer (pH 7.4, 140 mM NaCl, 2 mM $NaN_3$) as the eluting solvent. Aliquots of the resulting 1 mM lipid dispersion were diluted and incubated with appropriate concentrations of surfactant for 30 min at 23° C. and assayed for the release of carboxyfluorescein using the procedure described above.

| Compound No. | m | $n_{av}$ | $x_{av}$ |
|---|---|---|---|
| 1 | 10 | 13.6 | 6.0 |
| 2 | 10 | 22.7 | 7.4 |
| 3 | 14 | 13.6 | 8.1 |
| 4 | 14 | 22.7 | 6.0 |
| 5 | 20 | 22.7 | 7.4 |
| 6 | 14 | 13.6 | 3.5 |

The repeat unit/lipid ratio was calculated for each of compounds 1-6 and for comparative compounds 7 and Triton X-100 are shown in Table I.

Compound 7 was prepared by condensation of palmitoyl chloride with the corresponding poly(ethylene glycol) in $CHCl_3$/pyridine and was purified by flash chromatography on silica gel using $CHCl_3/CH_3OH$ (95/5, v/v).

TABLE I

| Surfactant-Induced Release of Liposome-Entrapped CF | |
|---|---|
| Surfactant | Repeat Unit/Lipid[a] |
| 1 | 0.33 |
| 2 | 132.00 |
| 3 | 0.03 |
| 4 | 0.12 |
| 5 | 6.67 |
| 6 | 0.05 |
| 7 | 0.42 |
| Triton X-100 | 6.67 |

[a]Molar ratio of repeat unit/lipid needed to release 50% of the entrapped 5(6)-carboxyfluorescein (CF); the lipid concentration was 3.4 μM.

Figure 7A:
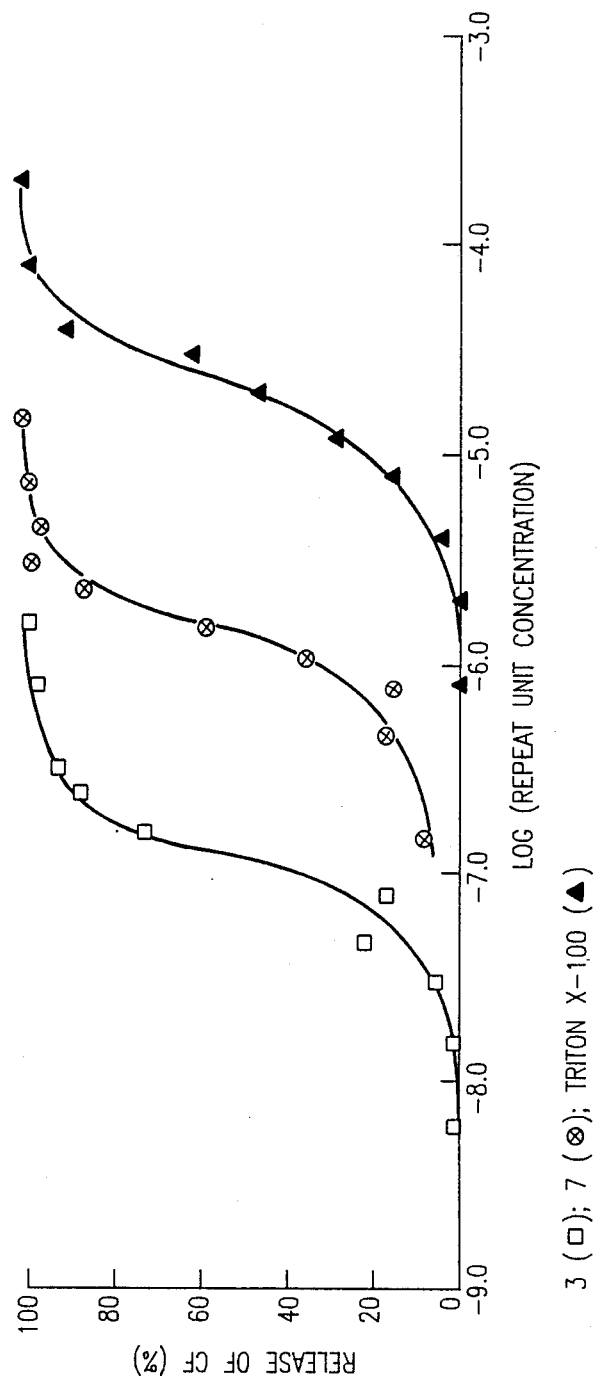
FIG. 7 *a* and 7 *b* are plots of the percentage of 5(6)-carboxyfluorescein released as a function of the repeat unit concentration for compounds 1–7 and Triton X-100.
Figure 7B:
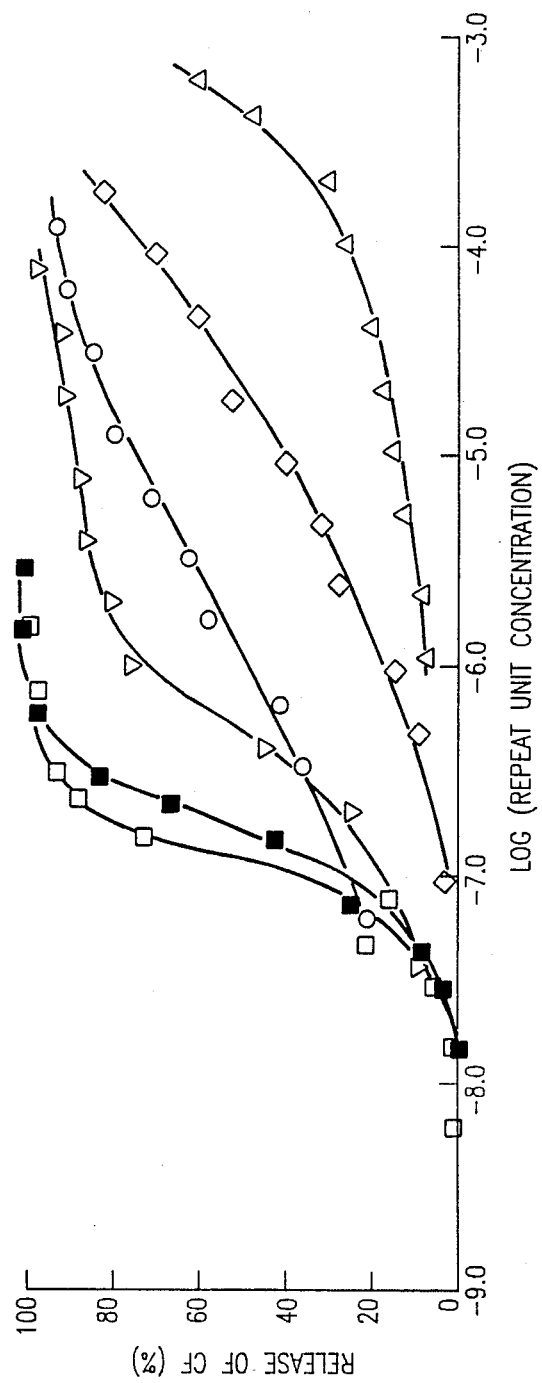

A comparison among compounds 1-6 indicates that supramolecular surfactants in which the dicarboxylic acid has 16 carbon atoms (m=14) and the poly(ethylene glycol) segments contains an average of 8.1 repeating units (n), wherein the overall surfactant contains an average of 13.6 repeating units (x) has particularly high membrane disrupting activity. That is, the number of repeat units per lipid required to release 50% of the liposome-entrapped carboxyfluorescein for compound 3 is very low as shown in Table I and illustrated in FIG. 7. Surprisingly, analogs such as compound 7 and Triton X-100 are substantially less active with regard to membrane disrupting activity.

The present compounds have also been tested by the National Cancer Institute (NCI) and evaluated for in vitro anti-HIV activity. The protocol used in NCI's Developmental Therapeutics Program AIDS anti-viral drug screening program involves plating of susceptible human "host" cells with and without virus in microculture plates, adding various concentrations of the test material, incubating the plates for seven days (during which time infected, non-drug treated control cells are largely or totally destroyed by the virus), and then determining the number of remaining viable cells using a colorimetric endpoint. There is a correlation between anti-HIV activity and the ability of the present supramolecular surfactants to disrupt lipid membranes. For example, Compounds 3 and 6 (see Table I) are particularly effective in releasing carboxyfluorescein and exhibit the best anti-HIV activity among Compounds 1-6 as well. The results of in vitro anti-HIV testing are shown in Table II.

TABLE II

| in vitro anti-HIV activity using cell line MT-2C | | |
|---|---|---|
| Compound No. | IC50* | EC50** |
| 1 | $>1.14 \times 10^{+2}$ | |
| 2 | $>1.07 \times 10^{+2}$ | |
| 3 | $>5.35 \times 10^{+1}$ | $1.45 \times 10^{+1}$ |
| 4 | $>1.07 \times 10^{+2}$ | |
| 5 | $>5.35 \times 10^{+1}$ | |
| 6 | $>1.42 \times 10^{+2}$ | $3.63 \times 10^{+1}$ |

*concentration (micrograms/milliliter) of drug resulting in 50% growth inhibition
**concentration (micrograms/milliliter) of drug resulting in 50% reduction of the viral cytopathic effect The pharmaceutical usefulness of the present compounds is enhanced by their low hemolytic activity. In contrast to their high potency for disrupting lipid bilayers, the compounds of the present invention show very poor hemolytic activity. Hemolytic activity was analyzed using known procedures (Miyajima K., Baba, T., Nakagaki, M., *Colloid & Polymer Sci.* 1987, 265, 943; Gabriel, N. E., Agman, N. V., Roberts, M. F., *Biochemistry*, 1987, 26, 7409). Using the standard procedure, 50% of the hemoglobin contained within $1.7 \times 10^8$ cells was released using 1.1 and 0.25 mM concentrations of compound 7 and Triton X-100 respectively after 30 minutes at 37° C. In contrast, with compound 6 of the present invention less than 1% of the hemoglobin was released using a repeat unit concentration of 4.5 mM. The compounds of the present invention, therefore, exhibit substantial lipid membrane disrupting activity with very low hemolytic activity.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An amphiphilic polymer, having the monomer unit structure A:

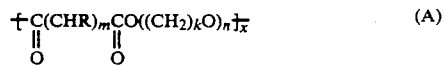

wherein R is at least one of H and $C_{1-6}$ alkyl, $k=1-4$, $m=10-30$, $n=12-50$ and $x=2-500$.

2. The amphiphilic polymer of claim 1, wherein $R=H$.
3. The amphiphilic polymer of claim 1, wherein $m=10-20$.
4. The amphiphilic polymer of claim 1, wherein $n=12-16$.
5. The amphiphilic polymer of claim 1, wherein x is 3-20.
6. The amphiphilic polymer of claim 1, wherein $m=12-30$.
7. The amphiphilic polymer of claim 1, wherein $m=12-18$.

* * * * *